United States Patent [19]

Noda et al.

[11] Patent Number: 4,870,090

[45] Date of Patent: Sep. 26, 1989

[54] THERAPEUTIC AGENT FOR THE TREATMENT OF DISORDERS ASSOCIATED WITH CEREBRAL ISCHEMIA

[75] Inventors: Yukifumi Noda, Shizuoka; Hiroyuki Nabata, Tokyo, both of Japan

[73] Assignee: Chugai Seiyaku Kabushiki Kaisha, Tokyo, Japan

[21] Appl. No.: 89,044

[22] Filed: Aug. 24, 1987

[30] Foreign Application Priority Data

Aug. 27, 1986 [JP] Japan ................................. 61-198796

[51] Int. Cl.⁴ ............................................ A61K 31/455
[52] U.S. Cl. .................................................... 514/355
[58] Field of Search ........................ 514/356, 355, 929

[56] References Cited

U.S. PATENT DOCUMENTS 4,200,640 4/1980 Nagano et al. ...................... 514/355
4,696,934 9/1987 Marcoux .............................. 514/277

FOREIGN PATENT DOCUMENTS 8606960 11/1986 PCT Int'l Appl. .
8705508 9/1987 PCT Int'l Appl. .
1562962 4/1976 United Kingdom .

OTHER PUBLICATIONS

Proceedings of the 10th Annual Meeting of the Japanese Cerebral Apoplexy Society, p. 116, (Apr. 18 and 19, 1985).
Proceedings of the 6th Annual Meeting of the Japanese Clinical Pharmacology Society, p. 83 (Nov. 28 and 30, 1985).
Program of the 8th International Congress of Neurological Surgery (Toronto, Jul. 7–13, 1985).
*Japanese Journal of Pharmacology* 37(1), pp. 124–128 (1985) Sakai et al.
*Japanese Heart Journal* 20(6) pp. 851–895 (1979) Nakajaura et al.
*Kekkan (Blood Vessel)* 6, p. 3 (1983).
*Japanese Heart Journal* 19 p. 112 (1977).
*Chiryou (Treatment)* 60, p. 1 (1978).
Stedmans Medical Dictionary, 24 Ed. (1983), p. 1352.

*Primary Examiner*—Douglas W. Robinson
*Assistant Examiner*—Richard Kearse
*Attorney, Agent, or Firm*—Browdy and Neimark

[57] ABSTRACT

An agent for the treatment of disorders associated with cerebral ischemia which comprises N-(2-hydroxyethyl) nicotinamide nitrate as an active ingredient.

6 Claims, No Drawings

THERAPEUTIC AGENT FOR THE TREATMENT OF DISORDERS ASSOCIATED WITH CEREBRAL ISCHEMIA

FIELD OF THE INVENTION

The present invention relates to a therapeutic agent for the treatment of disorders associated with cerebral ischemia, characterized in that it contains N-(2-hydroxyethyl) nicotinamide nitrate or a salt thereof as an active ingredient. More particularly, the present invention relates to a very effective agent for the treatment of disorders associated with cerebral ischemia, such as cerebral arteriosclerosis, sequela of cerebral infarction, sequela of cerebral hemorrhage, sequela of cerebral apoplexy, sequela of trauma in the head, etc. and symptoms related to these disorders, e.g., hypoxia, anoxia, etc., as well as neurological symptoms, such as vertigo, speech disturbance, motor and sensory disturbances, paropsis, etc.

PRIOR ART

N-(2-hydroxyethyl) nicotinamide nitrate has been used to treat patients suffering from angina pectoris. However, said compound has not been used to cure cerebral ischemia or related diseases.

On the other hand, various therapeutic agents are used for the treatment of disorders associated with cerebral ischemia covering both the acute and chronic phases. These agents are generally divided into the following two groups: ameliorants of cerebral circulation and activators of cerebral metabolism. While therapeutic agents classified as ameliorants of cerebral circulation generally have vasodilating effects on cerebral blood vessels, they have the same effects on the other peripheral blood vessels also, which lead to unfavorable outcomes such as systemic hypotension. Agents which act selectively on cerebral blood vessels, therefore, have been sought after. On the other hand, activators of cerebral metabolism are considered to ameliorate cerebral ischemia by increasing cerebral oxygen consumption and brain glucose intake, and also by exerting protective effects on the energy-producing system as is shown in ischemic experiments, although the mechanism of their action has not yet been clarified.

SUMMARY OF THE INVENTION

Only a few of the prior agents for the treatment of cerebral circulatory disorders have selective effects on cerebral blood vessels, and some of them cause systemic hypotension. In addition, the mechanism of the action of most of them is not known.

The present inventors have found that the compounds of the present invention, i.e., N-(2-hydroxyethyl) nicotinamide nitrate and salts thereof, dilate cerebral blood vessels without causing any substantial drop in systemic blood pressure [Kekkan (Blood Vessel) 6, 3 (1983), Japanese Heart Journal (Jap. Heart J.) 19, 112 (1977), and Chiryou (Treatment) 60, 1 (1978)]. In addition, they have found that these compounds enhance cerebral metabolism by increasing glucose intake by the brain, and that these compounds are effective in the treatment of various hypoxia models, and have thus completed this invention.

DETAILED DESCRIPTION OF THE INVENTION

Compounds of the present invention, N-(2-hydroxyethyl) nicotinamide nitrate and salts thereof may be prepared, for example, as described in the following:

To a nitrate ester of 2-aminoethanol, a catalyst such as sodium hydrogencarbonate, pyrimidine or a basic catalyst, e.g., potassium carbonate, triethylamine, etc. is added. The use of a catalyst is preferred although the reaction proceeds without one. Water or an organic solvent such as chloroform, pyridine, carbon tetrachloride, benzene, dichloromethane, toluene, triethylamine, etc., is added to the reaction mixture which is then cooled. While stirring, equal or excess molar nicotinic acid chloride, or its hydrochloride salt or another functional derivative of nicotinic acid, is added portionwise under heating or at room temperature, preferably between 0°-5° C. for 5-90 minutes, more preferably for 10-30 minutes. After stirring further and separating the solvent layer from the resulting product, the water layer is extracted again with the solvent. The combined solvent layer is washed and dried, followed by concentration under reduced pressure. The resulting residue is recrystallized from an organic solvent to give the object compound as colorless needle-like crystals.

This compound can optionally be converted to inorganic or organic salts such as hydrochloride salt, oxalate salt, p-toluenesulfonate salt, maleate salt, etc. by a routine method.

This therapeutic agent for the treatment of cerebral circulatory disorders can be administered to a human subject by appropriate methods such as an oral or parenteral (intramuscular, subcutaneous, intravenous, and suppository) method. The compound of the present invention can be formulated into such dosage forms as tablet, granule, powder, capsule, suspension, injection, suppository, etc. by a routine method in the field of formulation technology. For example, it can be formulated into tablet, granule, or powder by mixing it with an excipient, a binder, a solvent, etc., e.g., pharmaceutical excipients such as lactose, starch, mannitol, kaolin, crystalline cellulose, talc, calcium carbonate, magnesium stearate, etc. The compound can be also formulated into capsule either by filling a hard capsule with the compound in the form of granule or powder, or by filling a soft capsule with the oil-dissolved form of the compound. In the case of suspension formulation, the compound can be suspended in an aqueous solution together with gum arabic powder or white sugar followed by adjustment of its pH. In the case of injection formulation, the compound can be mixed with mannitol.

The content of the present compound in various dosage forms such as tablets, capsules, etc., should be an appropriate amount such that the therapeutic and prophylactic action of the compound of cerebral circulatory disorders will be effected without producing adverse effects. In general, it is convenient if each tablet or capsule contains 1-20 mg of this agent for the treatment of circulatory disorders as a dosage unit for oral administration and each vial contains about 0.1-12 mg of the same as a dosage unit for parenteral administration.

The actual dose to be administered to a patient using above unit dosage of the preparation depends on a patient's individual condition. Needless to say, it is necessary to change the actual dose according to the need of an individual patient. The appropriate daily dose for an adult patient is about 1-100 mg in the case of oral administration, and about 0.1-150 mg in the case of intraveneous injection.

EXAMPLE 1 (Preparation)

(a) Sublingual Tablet

| Compound of the present invention | |
|---|---|
| (free form) | 5 mg |
| Lactose | 19.7 mg |
| Mannitol | 25 mg |
| Magnesium stearate | 0.3 mg |
| | 50 mg/tablet |

The components listed above were mixed well and directly punched into tablets 50 mg in weight and 5 mm in diameter in a tableting machine.

(b) Tablet (for oral administration)

| Compound of the present invention | |
|---|---|
| (hydrochloride salt) | 10 mg |
| Lactose | 44.5 mg |
| Corn starch | 20 mg |
| Crystalline cellulose | 25 mg |
| Magnesium stearate | 0.5 mg |
| | 100 mg/tablet |

The components listed above were mixed well and directly punched into tablets 100 mg in weight and 7 mm in diameter in a tableting machine.

(c) Hard Capsule

| Compound of the present invention | |
|---|---|
| (free form) | 20 mg |
| Lactose | 176 mg |
| Magnesium stearate | 4 mg |
| | 200 mg/capsule |

The components listed above were mixed well and introduced into a capsule-filling machine to be charged into No. 3 capsules, so that each capsule would contain 200 mg of the mixture and weigh 250 mg as a whole.

(d) Granule (hard capsule)

| Compound of the present invention | |
|---|---|
| (free form) | 10 mg |
| Lactose | 710 mg |
| Corn starch glue | 280 mg |
| | 1,000 mg/package |

The components listed above were mixed and kneaded well. The mixture was formed into granules 1 mm in diameter using a granulator. They were charged into No. 3 capsule, so that each capsule would contain 200 mg of the granules and weigh 250 mg as a whole.

(e) Injection

| Compound of the present invention | |
|---|---|
| (free form) | 5 mg |
| Mannitol | 50 mg |
| | 55 mg/vial |

The components listed above were mixed well and charged into a suitable vial, followed by lyophilization by a routine method. The vial was then sealed to prepare an injection. The product is made to be dissolved in 1 ml of distilled water at the time of use for injection.

EXAMPLE 2 (Acute Toxicity)

The oral and intravaneous acute toxicities of the compound of the present invention were studied in male and female SD rats of 4 weeks old. The results showed that oral $LD_{50}$ is between 1,200 mg/kg and 1,300 mg/kg in both males and females, and that intravaneous $LD_{50}$ is between 800 mg/kg and 1,000 mg/kg in both males and females.

EXAMPLE 3 (Effects on Hypoxia or KCN-Induced Death)

(1) Animals and Drugs Used

Male F344/NS1c (Fischer) rats weighing 178-210 g (9 weeks old) were used in this study.

The test drug was suspended in 2% gum arabic solution and administered orally to the animals 30 minutes before the gas introduction or intravenous KCN injection. A control group similarly received 2.0 ml/kg of 2% gum arabic solution orally.

(2) Effect on Normobaric Hypoxia

Rats were placed in a cage under normal atmospheric pressure, and a mixture of gas consisting of 97% $N_2$ and 3% $O_2$ was introduced at the rate of 2 l/minute. The period from the start of gas introduction to the arrest of respiration was recorded as survival time (sec). Table 1 shows the results.

TABLE 1

| Test Drug | Dose (mg/kg) Administered Orally | Survival Time (sec) (mean ± S.E.) |
|---|---|---|
| Control | — | 311.8 ± 10.3 |
| Compound of the present invention | 3 | 357.4 ± 19.4 |
| | 10 | 446.5 ± 31.2*** |
| | 30 | 411.8 ± 28.6** |
| Nicardipine | 1 | 318.3 ± 9.6 |
| | 3 | 293.7 ± 15.3 |
| | 10 | 283.8 ± 14.4 |
| Vinpocetine | 10 | 348.3 ± 18.1 |
| | 30 | 367.8 ± 18.6* |
| | 100 | 371.4 ± 23.8* |

*$P < 0.05$,
**$P < 0.01$,
***$P < 0.001$ (Student's t-test)

(3) Effects on KCN-Induced Death

A group of 10 male rats (test drug group) and a group of 20 male rats (control group) were used. Thirty minutes after test drug administration, 3 mg/kg of KCN was administered from the caudal vein and the survival rate was recorded. The significance of survival rate data was tested by the $X^2$ method. Table 2 shows the results.

TABLE 2

| Test Drug | Dose (mg/kg) Administered Orally | Survival Rate (%) |
|---|---|---|
| Control | — | 3/20 (15.0) |
| Compound of the present invention | 3 | 2/10 (20.0) |
| | 10 | 3/10 (30.0) |
| | 30 | 8/10** (80.0) |
| Nicardipine | 1 | 0/10 (0.0) |
| | 3 | 0/10 (0.0) |
| | 10 | 3/10 (30.0) |
| Vinpocetine | 10 | 3/10 (30.0) |
| | 30 | 5/10 (50.0) |

TABLE 2-continued

| Test Drug | Dose (mg/kg) Administered Orally | Survival Rate (%) |
|---|---|---|
| | 100 | 7/10** (70.0) |

**P < 0.01

EXAMPLE 4 (Effects on Brain Glucose Intake)

(1) Animals and Drugs Used

Male F344/NS1c (Fischer) rats of 9-11 weeks old were used. They were subjected to study after about 18 hours of fasting.

The test drug was suspended in 2% gum arabic solution, and 2 ml/kg of it was administered orally to each group. The control group similarly received 2% gum arabic solution orally.

(2) Increase in Brain Glucose Intake in Normal Rats

The animals were divided into four groups, five per group. The compound of the present invention was administered orally to test groups at 3 dose levels, 3, 10 and 30 mg/kg; a control group received 2% gum arabic solution. Thirty minutes after the administration, the rats were killed by microwave irradiation (Toshiba microwave applicator, TMW-6402, 5 KW, 1.4 sec.) applied to the head. The skull was opened immediately, to excise the brain and the cerebral cortex was dissected out. Quantitative assay specimens were prepared according to the method of Forbergrova et al. [J. Neurochem., vol. 19 (1972)]. That is, to a weighed brain specimen, an ice-cooled 0.3 N-HClO$_4$/1 mM-EDTA solution was added (2 ml/200 mg wet tissue weight). The mixture was homogenized, and centrifuged (26,000×g, 10 minutes at 4° C.) to separate supernatant, which was stored. The obtained precipitate was homogenized and centrifuged again under the same conditions, and the supernatant was combined with the one obtained from the first centrifugation. The combined supernatant was neutralized with an ice-cooled mixture of 1.5 N KOH—0.4 M imidazole—0.3 N KCl, and after centrifugation, the resulting supernatant was used as samples for quantitative assay of glucose. The samples were assayed by a fluorophotometer (exciting wave length: 340 nm, fluorescent wave length 455 nm, Aminco Spectrophotofluorometer manufactured by American Institute Company), monitoring the formation and decomposition of NADH or NADPH. Table 3 shows the results.

TABLE 3

| Administered Drug | Dose (mg/kg P.O.) | N | Brain Glucose Level (μmol/g brain) (mean ± S.E.) |
|---|---|---|---|
| Control | — | 5 | 0.93 ± 0.06 |
| Compound of the present invention | 3 | 5 | 1.45 ± 0.07*** |
| | 10 | 5 | 1.53 ± 0.10*** |
| | 30 | 5 | 1.80 ± 0.08*** |

***P < 0.001 (Student's t-test)

(3) Increase in Brain Glucose Intake in Rats under Hypoxic Conditions

The animals received either 30 mg/kg of the compound of the present invention or 2% gum arabic solution (control) orally. Thirty minutes after the test drug administration, the rats where placed in a cage and a mixed gas consisting of 97% N$_2$ and 3% O$_2$ was introduced at a rate of 2 l/minute for 5 minutes to have them subjected to a hypoxic condition. Immediately after the hypoxic period, the rats were killed by microwave irradiation. The normal rats of the control group were killed by a similar method 30 minutes after the administration of the control solution. The cerebral cortex was dissected out and specimens for analysis were prepared as described in (1) and the glucose level was determined. Table 4 shows the results.

TABLE 4

| Administered Drug | Dose (mg/kg P.O.) | N | Brain Glucose Level (μmol/g brain) (mean ± S.E.) |
|---|---|---|---|
| Hypoxic condition | | | |
| Control | — | 8 | 0.92 ± 0.05 |
| Compound of the present invention | 30 | 8 | 1.12 ± 0.04** |
| Normal | | | |
| Control | — | 8 | 1.30 ± 0.03*** |

**P < 0.01,
***P < 0.001 (Student's t-test)

EXAMPLE 5 (Clinical Test)

Tablets containing the compound of the present invention were given orally at the daily dose 15-30 mg for 8 weeks to patients aged between 40 and 80 years old suffering from cerebral infarction (thrombosis or embolism) and cerebral arteriosclerosis. The alleviation of subjective and mental symptoms was evaluated (slight recovery - remarkable recovery) and the results are shown in Table 5.

TABLE 5

| Total No. of cases | No. of cases in which the treatment was effective (Effective Rate) |
|---|---|
| 49 | 33 (67.3%) |

As the only adverse reactions observed, mild headache was seen in two cases.

The results described above show that the compound of the present invention prolongs the survival time and increases the brain glucose intake in rats under hypoxic conditions. Thus, it is shown to be useful as a therapeutic agent for the treatment of disorders associated with cerebral ischemia.

What is claimed is:

1. A method for increasing brain glucose intake of a patient suffering from cerebral ischemia comprising administering to said patient an amount of Nicorandil effective to increase the brain glucose intake.

2. The method according to claim 1 wherein the cerebral ischemia is due to a condition selected from the group consisting of cerebral arteriosclerosis, sequela of cerebral infarction, sequela of cerebral hemorrhage, sequela of cerebral apoplexy, and sequela of trauma in the head.

3. The method according to claim 1 wherein the Nicorandil is administered at a rate of 2 mg/kg of body weight of the patient.

4. The method according to claim 1 wherein the Nicorandil is administered in the form of a tablet containing from 0.01 to 20 mg of Nicorandil.

5. The method according to claim 1 wherein the Nicorandil is administered in the form of a capsule containing 0.1 to 20 mg of Nicorandil.

6. The method according to claim 1 wherein the Nicorandil is administered in the form of an injection containing 1-12 mg of Nicorandil.

* * * * *